United States Patent [19]

Sharland

[11] 4,036,968

[45] July 19, 1977

[54] PHARMACEUTICAL TABLET

[75] Inventor: David Cedric Sharland, Worthing, England

[73] Assignee: Beecham Group Limited, England

[21] Appl. No.: 644,424

[22] Filed: Dec. 29, 1975

Related U.S. Application Data

[62] Division of Ser. No. 485,163, July 2, 1974, Pat. No. 3,996,365.

[30] Foreign Application Priority Data

July 12, 1973  United Kingdom .............. 33214/73

[51] Int. Cl.² ............................................. A61K 31/43
[52] U.S. Cl. .................................................... 424/271

[58] Field of Search ................................. 424/271, 166

[56] References Cited

PUBLICATIONS

The Merck Index, 8th Ed., Merck & Co., Inc., Rahway, N. J., 1968, pp. 271, 354 and 355.
Chemical Abstracts 58:1679f (1963).

*Primary Examiner*—Jerome D. Goldberg

[57] ABSTRACT

A pharmaceutical tablet which comprises at least 20 per cent by weight of one or more β-lactam antibiotics and from 0.1 to 4 parts by weight of urea per part of said β-lactam antibiotic.

6 Claims, No Drawings

PHARMACEUTICAL TABLET

CROSS-REFERENCE

This is a division of Ser. No. 485,163 filed July 2, 1974 now U.S. Pat. No. 3,996,365.

The present invention relates to pharmaceutical tablets containing urea and a β-lactam antibiotic.

In order to achieve high blood levels of antibiotic, it is desirable to include the antibiotic in a tablet which disperses rapidly in the stomach. It has now been discovered that if tablets are prepared which contain one or more β-lactam antibiotics and urea, excellent dissolution rates may be obtained in acidic media such as found in the stomach.

The present invention provides a pharmaceutical tablet comprising at least 20% by weight of one or more β-lactam antibiotics and from 0.1 to 4 parts by weight of urea per part of β-lactam antibiotic.

When used herein in reference to the present invention the term "β-lactam antibiotic" means active penicillins or cephalosporins.

Suitable β-lactam antibiotics for inclusion in the tablets of this invention include flucloxacillin, cloxacillin, dicloxacillin, carbenicillin α-monoesters, ticarcillin α-monoesters, phenoxymethyl penicillin, phenethicillin, benzylpencillin, benzylpenicillin acetoxymethyl ester, cephaloglycine, ampicillin phthalylyl ester, ampicillin pivaloyloxymethyl ester, ampicillin, amoxicillin and the like.

Usually the tablets of this invention will contain from 0.2 to 2 parts by weight of urea per part of β-lactam antibiotic.

Usually the tablets of this invention will contain from 10%–70% of urea and most usually from 20%–60% of urea.

Usually the tablets of this invention will weigh from 250 mg to 1,800 mg and usually from 300 mg to 1,700 mg.

One group of penicillins that benefit from inclusion in the tablets of this invention include those of formula (I):

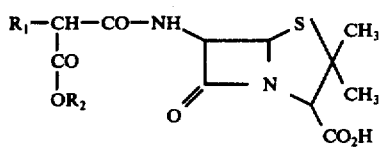

(I)

or a salt thereof wherein $R_1$ is a phenyl or thienyl group and $R_2$ is a group such that $CO_2R_2$ is an ester group. Normally $R_2$ is a hydrocarbon group of 1–10 carbon atoms such as the phenyl, toluyl or 5-indanyl group.

Particularly suitable compounds of formula (I) include the phenyl esters of carbenicillin or ticarcillin or their salts.

Salts of the compounds of formula (I) are preferably water soluble salts such as the sodium or potassium salts.

A further group of penicillins which benefit from inclusion in the tablets of this invention are those of formula (II):

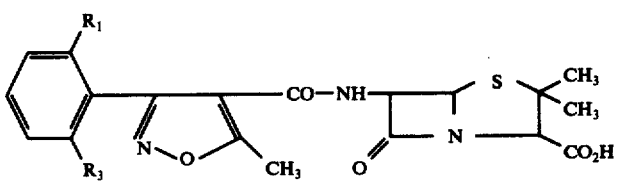

(II)

and their salts wherein $R_3$ is a hydrogen, chlorine or fluorine atom.

Particularly suitable compounds of the formula (II) include cloxacillin and flucloxacillin.

Salts of the compounds of formula (II) are preferably water soluble salts such as the sodium or potassium salts.

Particularly favored tablets of this invention which contain a compound of the formula (I) include those which comprise 25–60% of a water soluble salt of the phenyl or indanyl ester of carbenicillin and 40–75% of urea.

Such tablets frequently contain less than 10% of materials other than the antibiotic and urea.

Particularly suitable compounds for inclusion in such tablets are the phenyl esters of carbenicillin and ticarcillin and the indanyl ester of carbenicillin.

Most preferably this aspect of the invention consists of a tablet containing 25–60% of a water soluble salt of the phenyl ester of ticarcillin, 40–75% of urea and 0–10% of pharmaceutically acceptable tableting agents.

Tablets according to this invention frequently contain 50–800 mg of urea, for example 150–600 mg of urea.

Tablets according to this invention usually contain 250–750 mg of β-lactam antibiotic and 150–600 mg of urea.

As with other tablets, the tablets of this invention may contain pharmaceutically acceptable tableting agents such as lubricants, disintegrants, colours, surface active agents, buffers, preservatives and the like in conventional manner. However, when present such agents do not normally exceed 20% of the weight of the tablet and preferably do not account for more than 10% of the weight of the tablet.

It will be appreciated that as it is one of the objects of this invention to provide tablets with good disintegration rates the tablets of this invention do not contain substantial quantities of binders or fillers that are known to greatly retard the disintegration of tablets in the stomach.

Tablets of this invention usually have particularly good dissolution rates when they contain at least 50% of urea.

The tablets of this invention may be film coated if it is desired. Such film coatings are, of course, well known in the tabletting art and as in known tablets such coatings have the advantage of producing an esthetically pleasing, tasteless and stable tablet, but suffer from the disadvantage of slowing the disintegration rate. Thus, to maximize the advantages of this invention, film coatings, when present, should not consist of substantial amounts of acid insoluble materials.

The tablets of the invention may be prepared by blending together the ingredients and compressing in conventional manner. Film coatings may be applied after the formation of the tablet coat.

The tablets of the invention may frequently be prepared by direct compression (that is simply blend the materials and compress directly into tablets) although if desired a multiple compression technique may be employed (for example the materials apart from some lubricant may be blended together, compressed into slugs, reduced to granules, blended with further lubricant and compressed into granules).

An excipient almost always favorable in the tablets of this invention is a lubricant such as stearic acid or, more preferably, magnesium stearate.

It has been found that superior tablets result if the urea used in the preparation has been pretreated with methylene dichloride in order to modify its crystal form. Other solvents which may be used to partially modify the urea are mixtures of methylene dichloride and isopropyl alcohol or wetted methylene dichloride. Such partially modified urea does not generally produce such acceptable tablets.

An important aspect of this invention lies in the use of such modified urea in the preparation of pharmaceutical tablets.

It is highly preferable that this modified urea is used in the tablets of this invention as it generally results in the production of tablets with improved properties such as increased tablet strength.

The urea may be modified as follows: to 700g of urea was added sufficient methylene dichloride to wet all the crystals surfaces (about 500 ml) and the wetted crystals were then mixed in a planetary mixer for 5 minutes. The material was transferred to a forced air oven and dried for 2 hours at 70° C.

A suitable coat comprises an approximately 5:1:1 mixture of hydroxypropylmethyl cellulose, propylene glycol and titanium dioxide or color. Usually such materials are made to form a suspension in an organic solvent and sprayed onto the tablets which are then dried in a current of air.

In the following Examples dissolution rates were determined by stirring at 30 r.p.m. in a buffered solution at 37° C.

The following Examples illustrate the invention:

EXAMPLE 1

The sodium salt of β-phenoxycarbonylbenzylpenicillin was formulated into tablets having the following composition:

| Active compound | 528 mg |
| --- | --- |
| Urea | 712 mg |
| Magnesium Stearate | 20 mg |

The penicillin, urea and half the magnesium stearate were blended together, compressed into slugs, broken up into granules, blended with the rest of the magnesium stearate and recompressed into tablets.

EXAMPLES 2-4

Tablets were produced as in Example 1 in which the α-phenoxycarbonyl benzylpenicillin was replaced respectively by the sodium salts of the equivalent α-[2-isopropylphenoxycarbonyl] 5-indanyloxycarbonyl and α-[4-carbomethonylphenoxycarbonyl] compounds.

EXAMPLES 5-9

Tablets were produced as in Example 1 in which the quantities of ingredients (in mg) were as follows:

| Active Compound | 500 | 350 | 490 | 600 | 500 |
| --- | --- | --- | --- | --- | --- |
| Urea | 750 | 700 | 490 | 380 | 600 |
| Magnesium Stearate | 20 | 20 | 20 | 20 | 20 |
| Heavy Magnesium Carbonate | 0 | 0 | 0 | 0 | 200 |

EXAMPLE 10

Tablets were prepared as in Example 1 in which the carbenicillin ester was replace by an equal amount of (a) sodium benzylpenicillin or (b) sodium phenoxymethylpenicillin.

EXAMPLE 11

The sodium salt of α-phenoxycarbonyl benzyl penicillin was formulated into tablets having the composition:

| Active compound | 518 mg |
| --- | --- |
| Urea | 712 mg |
| Magnesium Stearate | 20 mg |
| | 1250 mg |

The tablets were produced by the slugging route and possessed the ability to release 90% of the drug within 13 minutes when tested at pH 2.5. Applying a film coat increased the $t_{90}$ to 27 minutes and when these tablets were tested under in-vivo conditions a urinary recovery of 50% was obtained within 6 hours. This compares to a maximum recovery of 56% obtained from a syrup. [$t_{90}$ is the time required for 90% of the medicament to be released]

EXAMPLES 12-15

Tablets were produced as in Example 11 in which the quantities of ingredients (in mgs) were as follows:

| Active compound | 518 | 518 | 518 | 258 |
| --- | --- | --- | --- | --- |
| Urea | 171.6 | 368.4 | 585.4 | 185.2 |
| Magnesium Sulphate | 10.4 | 13.6 | 16.6 | 6.8 |
| | 700 | 900 | 1200 | 450 |
| in vitro $t_{90}$ uncoated-mins | 17 | 15 | 12.5 | — |
| in vitro $t_{90}$ film coated-mins | 27 | 27 | 27 | 28 |
| in vivo urinary recovery 0–6 hours | 44% | 47% | — | — |

EXAMPLE 16

The phthalide ester of ampicillin was formulated via direct compression into tablets having the composition:

| Active compound | 399.4 mg |
| --- | --- |
| Magnesium Stearate | 10.6 mg |
| Sodium lauryl sulphate | 15.0 mg |
| Urea | 400.0 mg |
| | 825.0 mg |

At a pH of 1.5 these tablets gave an in-vitro dissolution of 90% within 12 minutes.

EXAMPLE 17

The sodium salt of cloxacillin was formulated via direct compression into tablets having the composition:

| | |
|---|---|
| Active compound | 573 mg |
| Urea | 67 mg |
| Magnesium Stearate | 10 mg |
| | 650 mg |

At a pH of 4.0 the tablets gave in-vitro drug dissolutions of 90% within 16 minutes.

EXAMPLE 18

The sodium salt of flucloxacillin was formulated via the direct compression route into tablets having the composition:

| | |
|---|---|
| Active material | 587 mg |
| Urea | 153 mg |
| Magnesium Stearate | 10 mg |
| | 750 mg |

At a pH of 4.0 the tablets gave in-vitro results of 9 minutes for 90% dissolution.

EXAMPLE 19

Two penicillins incorporated into a tablet have been produced to the formula:

| | |
|---|---|
| Amoxycillin Trihydrate | 603 mg |
| Sodium flucloxacillin | 587 mg |
| Urea | 400 mg |
| Magnesium Stearate | 10 mg |
| | 1600 mg |

Tablets prepared by the direct compression route yielded tablets giving an in-vitro total penicillin dissolution of 12.5 minutes for 90% at a pH of 4.0.

EXAMPLE 20

The use of a supporting buffer can be demonstrated with the phenyl ester of carbenicillin.

| | |
|---|---|
| Active Compound | 512 mg |
| Magnesium Stearate | 11 mg |
| Urea | 271 mg |
| Heavy Magnesium Carbonate | 120 mg |
| Primojel | 48 mg |
| Sodium lauryl sulphate | 8 mg |
| | 970 mg |

The tablets were produced by slugging together a blend of the penicillin urea and part of the magnesium stearate, reducing into granules, blending with the remaining materials and compressing into tablets. These tablets exhibited an in-vitro dissolution of 90% within 28 minutes at pH of 2.5.

EXAMPLE 21

Cephaloglycin was incorporated into tablets having the formulation:

| | |
|---|---|
| Cephalolycin dihydrate | 275.0 mg |
| Magnesium Stearate | 6.5 mg |
| Urea | 368.5 mg |
| | 650.4 mg |

Tablets prepared by direct compression produced times of 5 minutes for 90% dissolution at a pH of 1.5.

EXAMPLE 22

The sodium salt of the α-phenyl ester of ticarcillin was formed by the slugging route into tablets having the composition:

| | | | |
|---|---|---|---|
| Active compound | 500 | 500 | 300 |
| Urea | 170 | 300 | 190 |
| Magnesium stearate | 10 | 15 | 10 |

What we claim is:

1. A pharmaceutical tablet which comprises 10% to 70% urea and an antibacterially effective amount of at least 20% of a penicillin of the formula

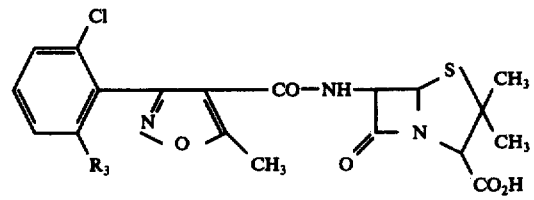

wherein $R_3$ is a hydrogen, chlorine or fluorine atom, or a pharmaceutically acceptable salt thereof.

2. A tablet according to claim 1 wherein the penicillin is cloxacillin or flucloxacillin.

3. A tablet according to claim 1, wherein the penicillin is the sodium or potassium salt of cloxacillin or flucloxacillin.

4. A tablet according to claim 1 which comprises 20% to 60% urea.

5. A tablet according to claim 1 which comprises at least 50% urea.

6. A tablet according to claim 1 wherein each tablet contains 150 to 600 mg of urea and 250 to 750 mg of the penicillin or sodium or potassium salt thereof.

* * * * *